US008889370B2

(12) United States Patent
Kappel et al.

(10) Patent No.: US 8,889,370 B2
(45) Date of Patent: Nov. 18, 2014

(54) METHOD OF DETERMINING INHIBITORS OF COAGULATION

(75) Inventors: Andreas Kappel, Koenigstein (DE); Andreas Rechner, Marburg (DE); Sina Stephan, Marburg (DE); Thomas Wissel, Lahntal (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 405 days.

(21) Appl. No.: 13/332,441

(22) Filed: Dec. 21, 2011

(65) Prior Publication Data

US 2012/0171697 A1 Jul. 5, 2012

(30) Foreign Application Priority Data

Dec. 30, 2010 (EP) ...................................... 10197337

(51) Int. Cl.
*G01N 33/00* (2006.01)
*C12Q 1/56* (2006.01)
*G01N 33/86* (2006.01)

(52) U.S. Cl.
CPC . *G01N 33/86* (2013.01); *C12Q 1/56* (2013.01)
USPC ........... 435/7.92; 435/7.1; 435/7.5; 435/7.93; 436/501; 436/518

(58) Field of Classification Search
None
See application file for complete search history.

(56) References Cited

U.S. PATENT DOCUMENTS

| | | | |
|---|---|---|---|
| 3,996,345 A | 12/1976 | Schwarzberg | |
| 5,627,038 A * | 5/1997 | Hemker | 435/7.21 |
| 8,304,205 B2 * | 11/2012 | Kappel et al. | 435/13 |
| 2006/0024834 A1 * | 2/2006 | Anslyn et al. | 436/93 |
| 2011/0091918 A1 * | 4/2011 | Christ et al. | 435/13 |
| 2012/0220617 A1 * | 8/2012 | Kraemer et al. | 514/279 |

FOREIGN PATENT DOCUMENTS

| | | |
|---|---|---|
| EP | 0034320 A1 | 8/1981 |
| EP | 0237332 A1 | 9/1987 |
| EP | 0456152 A2 | 11/1991 |
| EP | 0515194 A2 | 11/1992 |
| EP | 1918718 A1 | 5/2008 |
| EP | 2177624 A1 | 4/2010 |
| EP | 2177625 A1 | 4/2010 |
| WO | WO 9506877 A1 | 3/1995 |
| WO | WO 9629347 A1 | 9/1996 |

OTHER PUBLICATIONS

Ullman, E.F. et al., Luminescent oxygen channeling assay (LOCI): sensitive, broadly applicable homogeneous immunoassay method. Clinical Chemistry 1996, 42 (9), p. 1518-1526.; Magazine; 1996.
Claeson, G., Synthetic peptides and peptidomimetics as substrates and inhibitors of thrombin and other proteases in the blood coagulation system. Blood Coagulation and Fibrinolysis 1994, vol. 5, p. 411-436.; Magazine; 1994.
Nagahara, T. et al., Dibasic (amidinoaryl)propanoic acid derivatives as novel blood coagulation factor Xa inhibitors. J. Med. Chem. 1994, 37, p. 1200-1207.; Magazine; 1994.
Roehrig, S. et al., Discovery of the novel antithrombotic agent 5-chloro-N-(((5S)-2-oxo-3-(4-(3-oxomorpholin-4-yl) phenyl)-1,3-oxazolidin-5-yl) methyl)thiophene-2-carboxamide (BAY 59-7939): An oral, direct factor Xa inhibitor. J. Med. Chem. 2005, 48, p. 5900-5908.; Magazine; 2005.
Prasa, D. et al., Inhibition of thrombin generation in plasma by inhibitors of factor Xa. Thromb Haemost 1997, 78, p. 1215-1220.; Magazine; 1997.
Perzborn, E., Factor Xa inhibitors, New anticoagulants for secondary haemostasis. Hämostaseologie 2009, 29, p. 260-267.; Magazine; 2009.
Bartos, A. et al., New biotin derivatives for labeling and solubilizing IgG peptides. PeptideScience 2009, 92(2), p. 110-115.; Magazine; 2009.
Klebe, G., Wirkstoffdesign, Entwurf und Wirkung von Arzneistoffen, Second Edition 2009, Spektrum Akademischer Verlag Heidelberg; Book; 2009.
Dixon, M., The determination of enzyme inhibitor constants. Biochemical Laboratory 1953, 55, p. 170-171.; Magazine; 1953.
Prasa, D. et al., The ability of thrombin inhibitors to reduce the thrombin activity generated in plasma on extrinsic and intrinsic activation. Thrombosis and Haemostasis 1997, 77(3), p. 498-503.; Magazine; 1997.
Peula, J.M. et al., Covalent coupling of antibodies to aldehyde groups on polymer carriers. Journal of Materials Science: Materials in Medicine 1995; 6: 779-785.; Others; 1995.
Newman et al., "Particle Enhanced Light Scattering Immunoassay", Review Article—Ann Clin Biochem 1992; 29: 22-42.
Cauchon, Elizabeth et al., "Development of a Homogeneous Immunoassay for the Detection of Angiotensin I in Plasma Using AlphaLISA Acceptor Beads Technology," Analytical Biochemistry, vol. 388, No. 1, 6 pages, Mar. 1, 2009.

* cited by examiner

*Primary Examiner* — Gary W Counts
(74) *Attorney, Agent, or Firm* — King & Spalding L.L.P.

(57) ABSTRACT

A homogeneous method of determining inhibitors of proteolytically active coagulation factors (anticoagulants) in a sample, in particular direct thrombin and factor Xa inhibitors, and also a test kit to be used in such a method. Use is made of ligands which bind to the proteolytically active coagulation factor but are not cleaved by the latter and compete with the anticoagulant to be determined.

17 Claims, 8 Drawing Sheets

METHOD OF DETERMINING INHIBITORS OF COAGULATION

PRIORITY STATEMENT

The present application hereby claims priority under 35 U.S.C. §119 of European Patent Application Number 10197337.8 filed Dec. 30, 2010, the entire contents of which are hereby incorporated herein by reference.

FIELD OF INVENTION

The present invention is in the field of coagulation diagnostics and relates to a homogeneous method of determining inhibitors of proteolytically active coagulation factors (anticoagulants) in a sample, in particular direct thrombin and factor Xa inhibitors, and also to a test kit to be used in such a method.

BACKGROUND OF INVENTION

Common anticoagulant therapies primarily aim at inhibiting the procoagulatory factors thrombin (factor IIa, FIIa) and factor Xa (F Xa). A distinction is made between oral anticoagulation with vitamin K antagonists such as Coumadin, for example, which effects inhibition of coagulation factor synthesis, and anticoagulation due to inhibition of the active coagulation factors in the bloodstream. Among the anticoagulants which inhibit or inactivate active coagulation factors in the bloodstream, anticoagulants with direct action and anticoagulants with indirect action are distinguished. Anticoagulants with direct action such as, for example, rivaroxaban, dabigatran or melagatran bind to thrombin or factor Xa and are therefore highly specific. Anticoagulants with indirect action such as, for example, heparins bind to endogenous coagulation factor inhibitors such as antithrombin, for example, and amplify many times their anticoagulatory action.

All anticoagulants that inhibit active coagulation factors in the bloodstream are distinguished by a specific inactivation pattern. Certain classes of substances, for example unfractionated, high molecular weight heparins, inhibit both thrombin and factor Xa. Other substances act highly specifically, thus inhibiting either thrombin (e.g. hirudin, dabigatran, melagatran) or factor Xa (e.g. pentasaccharides such as fondaparinux, rivaroxaban).

Direct and indirect inhibitors of the central procoagulatory factors of the blood coagulation system, factor Xa and thrombin, increasingly play a part in the treatment and prevention of cardiovascular and thromboembolic disorders. These inhibitors can be detected by the currently established assays only in a very complex manner. A simple and sensitive assay for said substances would be important both for therapy monitoring and for detecting the presence of said substances in an unknown patient sample. These assays should be able to detect a relatively high number of structurally unrelated thrombin or F Xa inhibitors in a highly sensitive manner.

The chromogenic assays currently used for determining anticoagulants involve mixing the patient sample to be analyzed, which usually consists of plasma, with a substrate for a coagulation factor. Since most blood coagulation factors are serine endopeptidases, i.e. hydrolases which can cleave peptide bonds, use is made mainly of peptide substrates which are cleaved as specifically as possible by the blood coagulation factor to be determined and which have a detectable signal group. The established chromogenic assays which are also available commercially employ in particular the chromophores para-nitroaniline (pNA) and 5-amino-2-nitrobenzoic acid (ANBA), which have an absorbance peak at 405 nm. The yellow color produced is normally determined photometrically. With the determination of anticoagulants, the color concentration in the assay mix is inversely proportional to the anticoagulant concentration in the sample.

In a first group of currently applied chromogenic assays for determining anticoagulants which inhibit the activity of blood coagulation factors, the patient sample to be tested is usually admixed with a defined amount of an activated coagulation factor and with a substrate for this coagulation factor. The more anticoagulant is present in the sample, the more inhibition of the activated coagulation factor takes place and the less substrate is cleaved. Examples of commercially available assays based on this assay principle are the Berichrom® heparin assay by Siemens Healthcare Diagnostics for determining heparin on the basis of inhibition of added factor Xa, or the hirudin activity assay by Siemens Healthcare Diagnostics for determining hirudin on the basis of inhibition of added thrombin.

In a second group of currently applied chromogenic assays for determining anticoagulants, the patient sample to be tested is admixed with an inactive coagulation factor, a coagulation activator and with a chromogenic substrate for the coagulation factor. Addition of the coagulation activator initially activates the inactive coagulation factor added. The more anticoagulant is present in the sample, the more inhibition of the activated coagulation factor takes place and the less substrate is cleaved. Examples of commercially available assays based on this assay principle are the Haemosys®-ECA T assay from JenAffin for determining synthetic direct thrombin inhibitors, or the Haemosys®-ECA H assay from JenAffin for determining hirudin on the basis of inhibition of thrombin/meizothrombin which is formed in the sample due to the addition of prothrombin and ecarin as coagulation activator.

EP-A1-2 177 625 describes another assay principle of determining anticoagulants. This assay principle likewise involves determining the cleavage of a coagulation factor-specific substrate, but with the aid of a different kind of signal-producing system rather than with the aid of chromogenic substrates. Said system comprises two components which, when binding simultaneously to the intact substrate, interact due to close spatial proximity and generate a detectable signal, for example fluorescence or chemiluminescence. As a result of the cleavage of a peptide bond of the substrate, the two components are separated from one another, and therefore no signal is produced. The more anticoagulant is present in the sample, the more inhibition of the activated coagulation factor takes place, the less substrate is cleaved and the more signal is produced. The advantage of fluorescence- or chemiluminescence-based assays over the chromogenic assays is basically that they are more sensitive and also allow measurements in whole blood.

The method described above in which a cleavable substrate is to a certain extent "mounted" between the two components of the signaling system is disadvantageous in that the substrate ligand on both sides of the cleavage site must have regions for association with the signaling components. The substrate ligands are usually synthetic, low molecular weight peptide substrates which have two artificial residues for association with the signaling components, for example an amino terminal Flag tag and a carboxy terminal biotin residue. However, coupling of such residues to low molecular weight peptide substrates always bears the risk of altering the structure of the peptide in such a way that it is no longer bound or not cleaved by the enzyme to be detected, and providing suitable substrate ligands is therefore technically complex.

It is thus desirable to modify known methods of determining anticoagulants, which use two components interacting due to close spatial proximity and generating a detectable signal, in such a way that low molecular weight ligands can be used which need to have no more than one artificial residue for association with any of the signaling components.

This object is achieved by admixing an aliquot of a sample which is suspected of containing an anticoagulant with a defined amount of a proteolytically active coagulation factor and with a ligand which binds to the active site of the proteolytically active coagulation factor but is not cleaved thereby at a peptide bond, and measuring the signal generated by the signal-producing system as a result of binding of the ligand to the activated coagulation factor. The inhibitor of the activated coagulation factor, i.e. the anticoagulant, present in the sample competes in a concentration-dependent manner with the ligand for binding to the active site of the proteolytically active coagulation factor and consequently inhibits signal generation. The more anticoagulant is present in the sample, the less signal is generated.

SUMMARY OF INVENTION

The present invention therefore relates to a method of determining an inhibitor of a proteolytically active coagulation factor, i.e. an anticoagulant, in a sample, comprising the steps of:
a) providing and incubating a reaction mix comprising
  i. an aliquot of the sample,
  ii. a defined amount of a proteolytically active coagulation factor,
  iii. at least one ligand which binds to the active site of the proteolytically active coagulation factor but is not cleaved by the latter at a peptide bond,
  iv. a first and a second component of a signal-producing system which act together in such a way that a detectable signal is generated when said first and second components of said signal-producing system are brought into close proximity to each other, and wherein the proteolytically active coagulation factor is associated with the first component of the signal-producing system or will be associated therewith during incubation, and wherein the ligand is associated with the second component of the signal-producing system or will be associated therewith during incubation;
b) measuring the signal of the signal-producing system, wherein the amplitude of said signal is inversely proportional to the anticoagulant concentration in the sample.

BRIEF DESCRIPTION OF THE DRAWINGS

A more complete appreciation of the present invention and many of the attendant advantages thereof will be readily understood by reference to the following detailed description when taken in conjunction with the accompanying drawings, in which.

DETAILED DESCRIPTION OF INVENTION

Figure 1:
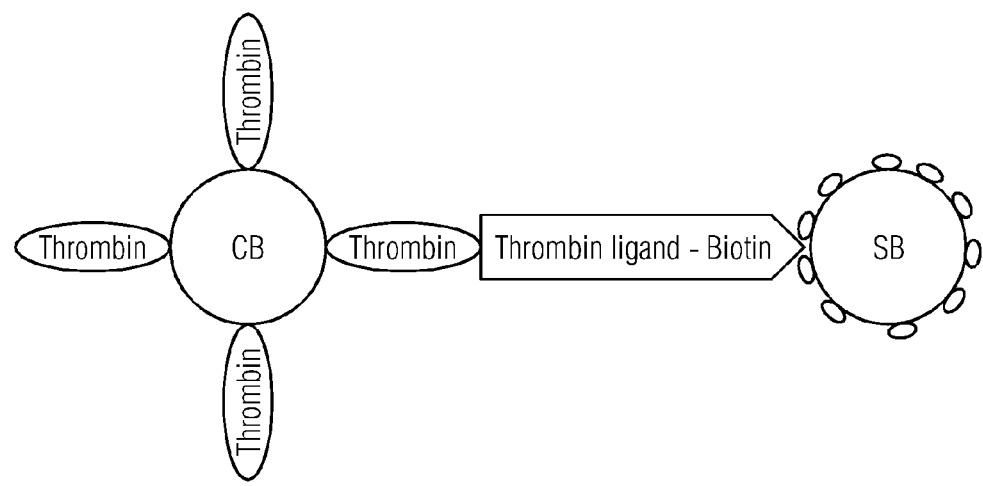
FIG. 1 shows a diagrammatic representation of an exemplary assay design for a method of the invention for determining thrombin inhibitors by means of LOCI technology.

The term "anticoagulant" is used in the context of the present invention for inhibitors of proteolytically active coagulation factors which are of natural or synthetic origin and the intended usage of which is inhibition of the coagulation system in vivo in humans or animals. This also includes high molecular weight substances such as hirudin or heparin which bind an enzyme at a plurality of binding sites, but also low molecular weight compounds such as rivaroxaban, dabigatran or melagatran, for which it is sufficient to bind only to the active site of the enzyme in order to inhibit reactivity. The terms "anticoagulant" and "inhibitor of a proteolytically active coagulation factor" are used synonymously for the purposes of the present invention.

The term "ligand" means in the context of the present invention substances which bind in the active site of a proteolytically active coagulation factor and which therefore compete with an inhibitor for the binding site. However, suitable ligands are not cleaved at a peptide bond by the proteolytically active coagulation factor because they lack a peptide bond cleavable by said proteolytically active coagulation factor, i.e. they do not have any peptidyl bond (R—CONH—R, R=amino acid residue) which can be hydrolyzed by the proteolytically active coagulation factor. Both reversibly and irreversibly binding ligands are suitable.

The ligand may be a synthetically, recombinantly or biotechnologically produced molecule or a naturally occurring molecule.

A ligand may be a peptide derivative, the sequence of which is derived from the sequence of a natural substrate of the enzyme. A peptide derivative ligand for the purposes of the present invention differs from a peptide substrate in that it is not hydrolytically cleaved by the proteolytically active coagulation factor, while the cleavage of a peptide substrate produces fragments which are released from the active site of the enzyme, and the enzyme re-emerges from the reaction unchanged.

Suitable peptide derivatives preferably comprise from 3 to about 150 amino acid residues. In order to be able to prevent the proteolytically active coagulation factor from cleaving a peptide derivative of the invention at a peptide bond, the carboxy terminal carboxyl group of the latter is preferably replaced with a functional group from the group consisting of aldehyde (—CHO), ketone (—COR; R=alkyl or aryl), trifluoromethyl ketone (—COCF$_3$), α-ketocarboxylic acid (—COCOOH), α-ketoamide (—COCONHR; R=alkyl or aryl), and α-keto ester (—COCOOR; R=alkyl or aryl), ester (—COOR; R=alkyl or aryl), boronic acid (—B(OR)$_2$), chloromethyl ketones (—COCH$_2$Cl), and sulfonyl fluorides (—SO$_2$F). The peptide derivative may have further structural modifications, for example partial usage of D-amino acids instead of naturally occurring L-amino acids.

Table 1 contains examples of typical functional groups for reversibly and irreversibly binding peptide derivative ligands.

TABLE 1

| Type of ligand | Functional group | |
| --- | --- | --- |
| irreversible | chloromethyl ketone | —COCH$_2$Cl |
| | sulfonyl fluoride | —SO$_2$F |
| | ester | —COOR |
| | | (R = alkyl or aryl) |
| | boronic acid | B(OR$_2$) |
| | | (R = alkyl or aryl) |
| reversible | aldehyde | —CHO |
| | ketone | —COR |
| | | (R = alkyl or aryl) |
| | trifluoromethyl ketone | —COCF$_3$ |
| | α-ketocarboxylic acid | —COCOOH |
| | α-ketoamide | —COCONHR |
| | | (R = alkyl or aryl) |
| | α-keto ester | —COCOOR |
| | | (R = alkyl or aryl) |

Examples of peptide derivative ligands which bind in the active site of thrombin but are not cleaved thereby at a peptide bond are:
H-D-Phe-Pro-Arg-H
Me-D-Phe-Pro-Arg-H
H-D-Phe-Pro-Agm
H-D-Phe-Pro-Arg-CH$_2$—Cl
H-D-Phe-Pro-Arg-CH$_2$F
Boc-DL-Dpa-Pro-Arg-H
Ac-D-Phe-Pro-boroArg pinanediol ester
D-Phe-Pro-NH—CH(methoxypropyl)-P(O)(OPh)$_2$ Examples of peptide derivative ligands which bind in the active site of factor Xa but are not cleaved thereby at a peptide bond are:
D-Arg-Gly-Arg-H
Dansyl-Glu-Gly-Arg-CH$_2$Cl Regarding the peptide derivative ligands mentioned, see also Claeson, G., Blood Coagulation and Fibrinolysis 5, 1994, 411-436.

A ligand may also be a compound which does not belong to the group of peptide compounds, such as, for example, an arginine ester, an amidinophenylalanine ester, a p-guanidinophenylalanine ester, a 3-amidinophenylalanine ester, a dibasic (amidinoaryl)propanoic acid derivative, or an oxazolidinone derivative.

Arginine derivative ligands which bind in the active site of thrombin but are not cleaved thereby at a peptide bond are, for example, Nα-arylsulfonylargininamides (R$_1$—SO$_2$-Arg-N—R$_2$/R$_3$; R$_1$=hydrophobic aliphatic or aromatic group) (Claeson, G., Blood Coagulation and Fibrinolysis 5, 1994, 411-436).

Amidinophenylalanine derivative ligands which bind in the active site of thrombin but are not cleaved thereby at a peptide bond are, for example, Nα-(β-naphthylsulfonyl-4-amidinophenylalanine piperidide or Nα-(β-naphthylsulfonyl-glycyl)-4-amidinophenylalanine piperidide (Claeson, G., Blood Coagulation and Fibrinolysis 5, 1994, 411-436).

A p-guanidinophenylalanine derivative ligand which binds in the active site of thrombin but is not cleaved thereby at a peptide bond is, for example, Tos-Gpa-piperidide (Claeson, G., Blood Coagulation and Fibrinolysis 5, 1994, 411-436).

A 3-amidinophenylalanine ester derivative ligand which binds in the active site of factor Xa but is not cleaved thereby at a peptide bond is, for example, Nα-(β-naphthylsulfonyl-glyclyl)-3-amidinophenylalanine (Claeson, G., Blood Coagulation and Fibrinolysis 5, 1994, 411-436).

A dibasic (amidinoaryl)propanoic acid derivative ligand which binds in the active site of factor Xa but is not cleaved thereby at a peptide bond is, for example, (2S)-2-[4[[(3S)-1-acetimidoyl-3-pyrrolidinyl]oxy]phenyl]-3-(7-amidino-2-naphthyl)propanoic acid (Nagahara, T. et al., J. Med. Chem. 1994, 37, 1200-1207).

An oxazolidinone derivative ligand which binds in the active site of factor Xa but is not cleaved thereby at a peptide bond is, for example, 5-chloro-N-({(5S)-2-oxo-3-[4-(3-oxo-morpholin-4-yl)phenyl]-1,3-oxazolidin-5-yl}methyl) thiophene-2-carboxamide (Roehrig, S., et al., J. Med. Chem. 2005, 48(19), 5900-5908).

A reversibly binding ligand means a ligand which can be displaced in a concentration-dependent manner by at least one natural or synthetic inhibitor from the active site of the proteolytically active coagulation factor.

Examples of suitable ligands binding reversibly to thrombin are peptide derivatives such as, for example, H-D-Phe-Pro-Arg-H, Me-D-Phe-Pro-Arg-H or H-D-Phe-Pro-Agm. The carboxyl group in agmatine (Agm) has been replaced with hydrogen. Other ligands binding reversibly to thrombin are Nα-arylsulfonylargininamide (R$_1$—SO$_2$-Arg-N—R$_2$/R$_3$) or amidinopiperidine derivatives such as Nα-(β-naphthylsulfonyl)-4-amidinophenylalanine piperidide, or derivatives of p-guanidinophenylalanine (Gpa), amidinophenylalanine (Apa), for example Tos-Gpa-piperidide and Tos-Apa-piperidide, or else peptide aminoboronic acids or peptide aminophosphonic acids, for example Ac-D-Phe-Pro-NH—CH(CH$_2$-phenyl)-B—OPin and D-Ala-Pro-NH—CH(methoxypropyl)-P(O)(OPh)$_2$.

Examples of suitable ligands binding reversibly to factor Xa are peptide derivatives such as, for example, D-Arg-Gly-Arg-H or benzamidine derivatives and 3-amidinophenylalanine esters such as, for example, Nα-(β-naphthylsulfonyl-glyclyl)-3-amidinophenylalanine.

An irreversibly binding ligand means a ligand which binds in a concentration-independent manner to the active site of the proteolytically active coagulation factor and which can no longer be displaced because it forms, for example, a covalent bond with the enzyme and modifies the enzyme in such a way that the active site is irreversibly inactivated. Typical irreversibly binding ligands consist of a part which introduces them into the active site of the enzyme and of a chemically reactive group which is capable of forming covalent bonds with the enzyme, i.e. with the hydroxyl function of the serine in the active site in the case of the proteolytically active coagulaton factors. To form the covalent bond with the enzyme, a part of the functional group is removed from the ligand which then, in the same reaction step, binds covalently to the enzyme.

Examples of suitable ligands binding irreversibly to thrombin are H-D-Phe-Pro-Arg-CH$_2$—Cl and H-D-Phe-Pro-Arg-CH$_2$F.

An example of a suitable ligand binding irreversibly to factor Xa is dansyl-Glu-Gly-Arg-CH$_2$Cl.

Reversibly and irreversibly binding ligands can be distinguished by their reaction kinetics. Plotting 1/v, where v is the reaction rate, as a function of the ligand concentration (i) at constant substrate concentration (S) produces a straight line.

When two or more different substrate concentrations ($S_1$, $S_2 \ldots S_N$) are used, the lines intersect at a single point. The x axis value of this point corresponds to $-K_i$, with $K_i$ corresponding to the binding constant, see FIG. 3, detail (Dixon, M., 1953, Biochem J, 55, 170-171). With irreversible inhibition, the curves meet at a single point on the x axis which again corresponds to $-K_i$.

Preferred ligands have a binding affinity to the proteolytically active coagulation factor which corresponds to or is lower than the affinity of the anticoagulant to be determined. Thrombin inhibitors used as anticoagulants exhibit a binding constant for thrombin in the range from $2.7 \times 10^{-14}$ mol (hirudin) to $1.9 \times 10^{-8}$ mol (argatroban) (Prasa, D. et al., Thromb Haemost 77, 1997, 498-503). Aside from thrombin, the thrombin inhibitors also bind F Xa, albeit with substantially lower affinity, i.e. with a larger binding constant of $2.1 \times 10^{-4}$ mol, for example argatroban (Prasa, D. et al., Thromb Haemost 78, 1997, 1215-1220). F Xa inhibitors have a binding constant in the range from $8 \times 10^{-11}$ mol (apixaban) to $6.6 \times 10^{-9}$ mol (LY517717 difumarate), with said F Xa inhibitors also binding to thrombin to a certain extent but up to 10 000 times more weakly, for example for rivaroxaban (Perzborn, E., Hämostaseologie 3, 2009, 260-267). Reversible ligands can thus be displaced by the inhibitor to be determined from the active site of the proteolytically active coagulation factor. Irreversible ligands with an appropriately selected affinity cannot thus displace the medicament to be determined from the active site of the proteolytically active coagulation factor within a relevant period of time. On the other hand, the affinity must not be too low because otherwise no signal can be produced.

The binding constant of suitable ligands is therefore preferably in a range from 0.0001 to 100 000 nM ($10^{-13}$ to $10^{-4}$ M), particularly preferably in a range from 0.1 to 10 000 nM ($10^{-10}$ to $10^{-5}$ M), very particularly preferably in a range from 1 to 1000 nM ($10^{-9}$ to $10^{-6}$ M).

The term "sample" means for the purposes of the present invention the material which is suspected to contain the anticoagulant to be detected. The term "sample" comprises in particular biological fluids or tissues of humans and animals, such as blood, plasma, serum, and also other body fluids, excreta or extracts.

The method of the invention comprises providing and incubating a reaction mix comprising an aliquot of the sample, a defined amount of a proteolytically active coagulation factor, at least one ligand which binds to the active site of the proteolytically active coagulation factor but is not cleaved thereby at a peptide bond, a first and a second component of a signal-producing system which interact in such a way that a detectable signal is produced when said first and second components of said signal-producing system are brought into close proximity to each other. The proteolytically active coagulation factor is associated with or, during incubation, will be associated with the first component of the signal-producing system. The ligand is associated with or, during incubation, will be associated with the second component of the signal-producing system. As a result of the ligand binding to the active site of the proteolytically active coagulation factor, the components of the signal-producing system are brought into close proximity to each other, whereby a detectable signal is produced which correlates with the activity of the proteolytically active coagulation factor in the reaction mix. The anticoagulant present in the sample competes in a concentration-dependent manner with the ligand which cannot be cleaved at a peptide bond for binding to the active site of the proteolytically active coagulation factor and, as a result, inhibits signal generation. The more anti-coagulant is present in the sample, the less signal is generated. The signal produced is measured, with the amplitude of the signal being inversely proportional to the anticoagulant concentration in the sample.

The method of the invention is suitable for determining inhibitors of the proteolytically active coagulation factors thrombin (factor IIa), factor VIIa, factor IXa, factor Xa, factor XIa or factor XIIa.

Which activated coagulation factor and which ligand are added to the reaction mix depends on the specificity of the anticoagulant to be determined.

The addition of thrombin or of factor Xa and the addition of a ligand having thrombin or factor Xa specificity are particularly suitable for determining a heparin, i.e. a high molecular weight, unfractionated heparin (HMW heparin) or a low molecular weight heparin (LMW heparin) or a heparinoid. The addition of factor IIa (thrombin) and the addition of a ligand having thrombin specificity are particularly suitable for determining a direct thrombin inhibitor, for example argatroban, melagatran, ximelagatran, bivalirudin, dabigatran, hirudin, lepirudin, MCC-977, SSR-182289, TGN-255, TGN-167, ARC-183 and odiparcil. The addition of factor Xa and of a factor Xa-specific ligand is particularly suitable for determining a direct factor Xa inhibitor, for example rivaroxaban; apixaban; otamixaban, which are combined in the new active substance class of xabanes; fondaparinux; LY 517717; YM 153; DU-176b; DX-9065a and KFA-1982.

The proteolytically active coagulation factor added to the reaction mix may be a coagulation factor which has been isolated from animal or human tissue or body fluids, for example blood or plasma, or which has been isolated from supernatants or lysates of animal or human cell cultures or of cultures of eukaryotic cells or of microorganisms such as bacteria or fungi which express a recombinant coagulation factor. Methods of activating initially inactive zymogens of the various coagulation factors are well known to the skilled worker. Which activated coagulation factor is added to the reaction mix depends on the anticoagulant that is to be determined.

In one embodiment of the method of the invention, the proteolytically active coagulation factor has a first binding partner X of a binding pair X/Y, and the first component of the signal-producing system is associated with the second binding partner Y of said binding pair X/Y, whereby the proteolytically active coagulation factor, due to binding of the binding partners X and Y, is bound to the first component of the signal-producing system or will be bound to the first component of the signal-producing system during incubation of the reaction mixture.

The binding partners X and Y are two different molecules which specifically recognize and bind each other. Examples of specific recognition and binding are antibody-antigen interactions, polynucleotide interactions, etc.

Suitable binding pairs X/Y are especially antigen/antibody combinations, with the binding partner X being an antigenic epitope of the proteolytically active coagulation factor. The antigenic epitope may be a natural sequence epitope or structural epitope of the natural protein. The antigenic epitope may also be a heterologous sequence epitope or structural epitope of a modified active coagulation factor. Examples of heterologous sequence or structural epitopes are FLAG, or HIS or fluorescein tags which are used in particular for labeling peptides or proteins. Other suitable binding pairs X/Y are complementary polynucleotides X and Y. The binding partner Y associated with the first component of the signal-producing system must be chosen so as to enable proteolytically active coagulation factor to be specifically bound. The binding partner Y preferably consists of an antibody or an antigen-binding fragment thereof. Particularly preferred binding pairs X/Y are FLAG tag/anti-FLAG tag antibody, HIS tag/anti-HIS tag antibody, fluorescein/anti-fluorescein antibody, biotin/avidin, and biotin/streptavidin.

In another embodiment of the method of the invention, the proteolytically active coagulation factor is connected to the first component of the signal-producing system via a covalent bond.

In a preferred embodiment, the ligand which is added to the reaction mix has a first binding partner A of a first binding pair A/B for binding to the second component of the signal-producing system, which component appropriately has the second binding partner B of said binding pair A/B. Particularly preferably, the ligand has at least one biotin residue as binding partner A.

The binding partners A and B are two different molecules which specifically recognize and bind each other. Examples of specific recognition and binding are antibody-antigen interactions, polynucleotide interactions, etc.

Suitable binding pairs A/B are especially antigen/antibody combinations, with the binding partner A being an antigenic epitope of the ligand. The antigenic epitope may be a natural sequence epitope or structural epitope of a natural protein or protein fragment. The antigenic epitope may also be a heterologous sequence epitope or structural epitope of a modified peptide. Examples of heterologous sequence or structural epitopes are FLAG, or HIS or fluorescein tags which are used in particular for labeling low molecular weight substances, peptides or proteins. Further suitable binding pairs A/B are complementary polynucleotides A and B. The binding partner B associated with the second component of the signal-producing system must be chosen in such a way that the ligand can be bound specifically. Preferably, the binding partner B consists of an antibody or an antigen-binding fragment thereof. Particularly preferred binding pairs A/B are FLAG tag/anti-FLAG tag antibody, HIS tag/anti-HIS tag antibody, fluorescein/anti-fluorescein antibody, biotin/avidin, and biotin/streptavidin.

A possible binding pair A/B for associating the ligand with the second signaling component must in principle be chosen in such a way that it does not interfere, due to mutual binding, with a possible binding pair X/Y for associating the proteolytically active coagulation factor with the first signaling component.

One advantage of the present invention is that the ligand used can, but does not need to, have a second artificial binding partner of a binding pair.

The term "signal-producing system" means for the purposes of the present invention a system which comprises at least a first and a second component which interact in such a way that a detectable signal is produced when they are brought into close proximity to each other.

In one embodiment, the components of the signal-producing system are particulate solid phases, for example latex particles, the agglutination of which is determined turbidimetrically or nephelometrically. For this purpose, the first component of the signal-producing system consists of a first particulate solid phase whose nature is such that it is associated or associable with the proteolytically active coagulation factor. The first particulate solid phase may be connected to the proteolytically active coagulation factor via a covalent bond or via a binding pair X/Y or will be able to be connected thereto via a binding pair X/Y in the reaction mix. Furthermore, the second component of the signal-producing system consists of a second particulate solid phase whose nature is such that it is associated or associable with the ligand. The second particulate solid phase can be connected via a covalent bond or via a binding pair A/B to the ligand or will be able to be connected thereto via a binding pair A/B in the reaction mix. Immunoassays based on the principle of particle-enhanced light scattering have been known since about 1920 (for an overview, see Newman, D. J. et al., Particle enhanced light scattering immunoassay. Ann Clin Biochem 1992; 29: 22-42). Preference is given to using polystyrene particles of from 0.1 to 0.5 µm, particularly preferably from 0.15 to 0.35 µm in diameter. Preference is given to using polystyrene particles having carboxyl or aldehyde functions. Preference is furthermore given to using shell/core particles. Synthesis of said particles and covalent coupling of ligands are described, for example, in Peula, J. M. et al., Covalent coupling of antibodies to aldehyde groups on polymer carriers. Journal of Materials Science Materials in Medicine 1995; 6: 779-785.

In another embodiment of the method of the invention, the signal-producing system comprises at least a first and a second component which interact in such a way that a detectable signal is produced when they are brought into close proximity to each other and can therefore interact with one another. An interaction between said components means in particular an energy transfer—that is, the direct transfer of energy between the components, for example by way of light or electron radiation and via reactive chemical molecules such as, for example, short-lived singlet oxygen. Energy may be transferred from one component to another but it is also possible for a cascade of various substances to conduct energy transfer. For example, the components may be a pair consisting of an energy donor and an energy acceptor, such as, for example, photosensitizer and chemiluminescent agent (EP-A2-0515194, LOCI® Technologie) or photosensitizer and fluorophore (WO 95/06877) or radioactive iodine <125> and fluorophore (Udenfriend et al. (1985) Proc. Natl. Acad. Sci. 82: 8672-8676) or fluorophore and fluorescence quencher (U.S. Pat. No. 3,996,345).

The first component and/or the second component of the signal-producing system, which can interact with one another, can be associated covalently or via a specific interaction with a particulate solid phase or be embedded therein. The term particulate solid phase means suspendable particles such as, for example, metal sols, silica particles, magnetic particles or, particularly preferably, latex particles. Preference is given to particles of 0.01-10 micrometers in diameter, with particular preference being given to particles of 0.1-1 micrometer in diameter.

The first component of the signal-producing system whose components interact in such a way that a detectable signal is produced when they are brought into close proximity to each other and as a result can interact with one another, is of such a nature that it is associated or associable with the proteolytically active coagulation factor. The first component of the signal-producing system may be associated or associable directly with the proteolytically active coagulation factor. Preference is given to the first component of the signal-producing system being associated or associable indirectly with the proteolytically active coagulation factor. For this purpose, the first component of the signal-producing system is associated with a particulate solid phase which additionally is associated covalently or via a binding pair X/Y or is associable via a binding pair X/Y with the proteolytically active coagulation factor.

The second component of the signal-producing system whose components interact in such a way that a detectable signal is produced when they are brought into close proximity to each other and as a result can interact with one another, is of such a nature that it is associated or associable with the ligand. The second component of the signal-producing system may be associated or associable directly with the ligand. Preference is given to the second component of the signal-producing system being associated or associable indirectly with the ligand. For this purpose, the second component of the signal-producing system is associated with a particulate solid phase which additionally is associated covalently or via a binding pair A/B or is associable via a binding pair A/B with the ligand.

In a preferred embodiment of the method of the invention for determining an inhibitor of a proteolytically active coagulation factor, the sample is additionally admixed with a fibrin aggregation inhibitor. Fibrin aggregation inhibitors are substances which prevent aggregation of thrombin-induced fibrin monomers. This prevents the development of a fibrin clot in a fibrinogen-containing sample, which could otherwise have a negative impact on the measurement, for example by limiting diffusion and quenching. Preferred fibrin aggregation inhibitors are synthetic peptides, for example a peptide of the sequence glycine, proline, arginine, proline (commercially available as Pefabloc® FG, Pentapharm, Switzerland). Further preferred peptides which may be used as fibrin aggregation inhibitors, in particular the preferred peptide of the sequence glycine, proline, arginine, proline, alanine, are described in EP-A2-456 152.

In a preferred embodiment of the method of the invention for determining a direct inhibitor of a proteolytically active coagulation factor, additionally a polyamine such as Polybrene® (hexadimethrine bromide), spermine or polylysine is added to the reaction mix. Polyamines inhibit indirect inhibition of the coagulation factor by heparins. In this way, the method of the invention can be used to distinguish between heparin-induced and direct inhibition.

After the reaction mix containing the sample, a defined amount of a proteolytically active coagulation factor, at least one ligand which binds to the active site of the proteolytically active coagulation factor but is not cleaved thereby at a peptide bond, and a first and second component of a signal-producing system has been provided, the reaction mixture is incubated for a limited time in order to ensure sufficient association of proteolytically active coagulation factor, anticoagulant and ligand and, where appropriate, of the first signaling component with the proteolytically active coagulation factor and/or of the second signaling component with the ligand. The term "sufficient" should be understood as meaning that the method as a whole enables an inhibitor of a proteolytically active coagulation factor to be determined in a quantitative manner. The optimal incubation time of a particular assay design can be determined experimentally. The reaction mix may be provided in several individual steps in a different order and with different incubation times.

The signal or signal change as a function of time, which is produced in the reaction mixture, correlates with the activity or amount of the inhibitor of the proteolytically active coagulation factor. The activity or amount of an inhibitor of the proteolytically active coagulation factor can be established via said correlation with the aid of said signal or signal change over time. To this end, preference is given to carrying out a calibration using a standard. Said standard possesses a defined activity or amount of the inhibitor of the proteolytically active coagulation factor.

The present invention further relates to test kits for carrying out the various embodiments of the method of the invention.

A first test kit comprises the following separate components:
a first reagent comprising a defined amount of a proteolytically active coagulation factor;
a second reagent comprising at least one ligand which binds to the active site of the proteolytically active coagulation factor but is not cleaved by the latter at a peptide bond;
a third reagent comprising a first component of a signal-producing system, which component is associable with the proteolytically active coagulation factor from the first reagent; and
a fourth reagent comprising a second component of a signal-producing system, which component is associable with the ligand from the second reagent.

When using such a test kit, each component is added individually to the sample or the reaction mix, and association of the proteolytically active coagulation factor with the first component of the signal-producing system and association of the ligand with the second component of the signal-producing system take place during incubation in the reaction mix. The advantage of this is that the third and fourth reagents may in each case be a universally employable detection reagent, if the proteolytically active coagulation factor and the ligand, respectively, are associated via conventional binding pairs A/B and X/Y, respectively, for example via streptavidin/biotin, avidin/biotin, FLAG tag/anti-FLAG tag antibody or the like.

Another test kit comprises the following separate components:
a first reagent comprising a defined amount of a proteolytically active coagulation factor, wherein the proteolytically active coagulation factor is associated with a first component of a signal-producing system;
a second reagent comprising at least one ligand which binds to the active site of the proteolytically active coagulation factor but is not cleaved by the latter at a peptide bond; and
a third reagent comprising a second component of the signal-producing system, which component is associable with the ligand from the second reagent.

When using such a test kit, only association of the ligand with the second component of the signal-producing system takes place during incubation in the reaction mix; the proteolytically active coagulation factor is already associated with the first component of the signal-producing system.

Yet another test kit comprises the following separate components:
a first reagent comprising a defined amount of a proteolytically active coagulation factor;
a second reagent comprising a first component of a signal-producing system, which component is associable with the proteolytically active coagulation factor from the first reagent; and
a third reagent comprising at least one ligand which binds to the active site of the proteolytically active coagulation factor but is not cleaved by the latter at a peptide bond, and wherein the ligand is associated with a second component of the signal-producing system.

When using such a test kit, only association of the proteolytically active coagulation factor with the first component of the signal-producing system takes place during incubation in the reaction mix; the ligand is already associated with the first component of the signal-producing system.

Yet another test kit comprises the following separate components:
a first reagent comprising a defined amount of a proteolytically active coagulation factor, wherein the proteolytically active coagulation factor is associated with a first component of a signal-producing system; and
a second reagent comprising at least one ligand which binds to the active site of the proteolytically active coagulation factor but is not cleaved by the latter at a peptide bond, and wherein the ligand is associated with a second component of the signal-producing system.

When using such a test kit, both the proteolytically active coagulation factor and the ligand are already associated with the particular components of the signal-producing system.

The advantage, among others, of test kits in which the proteolytically active coagulation factor and/or the ligand are already associated with the particular signaling component, is that the number of the reagents to be used is minimized, thereby avoiding pipetting steps and reducing the risk of pipetting errors.

LIST OF ABBREVIATIONS

Ac Acyl-
Agm Agmatine
Ala Alanine
ANBA 5-Amino-2-nitro-benzoic acid
Arg Arginine
B-f-P—R—H Biotinyl-Ttds-D-Phe-Pro-Arg-H
Boc tert-Butyl carbonate
B-r-P—R—H Biotinyl-Ttds-D-Arg-Pro-Arg-H
Dpa β,β-Diphenylalanine
f D-Phenylalanine
Gly Glycine
Gpa Guanidinophenylalanine
His Histidine
IPA Isopropylamide
Ki Binding constant
Me Methyl-
Ph Phenyl-
Phe Phenylalanine
pNA para-Nitroaniline
Pro Proline
r D-Arginine
R Correlation coefficient
Tos Tosyl-
Ttds 4,7,10-Trioxa-1,13-tridecanediaminosuccinic acid
Z-D-Leu Carbobenzoxy-D-leucine FIG. 1 shows a diagrammatic representation of an exemplary assay design for a method of the invention for determining thrombin inhibitors by means of LOCI technology. Proteolytically active thrombin is bound to a particulate solid phase which is also coated with a chemiluminescent agent (Chemibead, CB). The second component of the signal-producing system consists of a particulate solid phase which is coated with a photosensitizer and also with streptavidin (Sensibead, SB). A ligand which binds to the active site of thrombin but is not cleaved thereby and which has a biotin label that binds to the streptavidin of the Sensibead brings the two components of the signal-producing system into close spatial proximity. The excitation of the photosensitizer with light causes short-lived singlet oxygen to be produced which is able to activate the chemiluminescent agent, whereby a luminescence signal is emitted. The more thrombin inhibitor (anticoagulant) which competes with the noncleavable, biotinylated ligand for binding to thrombin is present in a sample, the less luminescence signal is generated.

Figure 2:
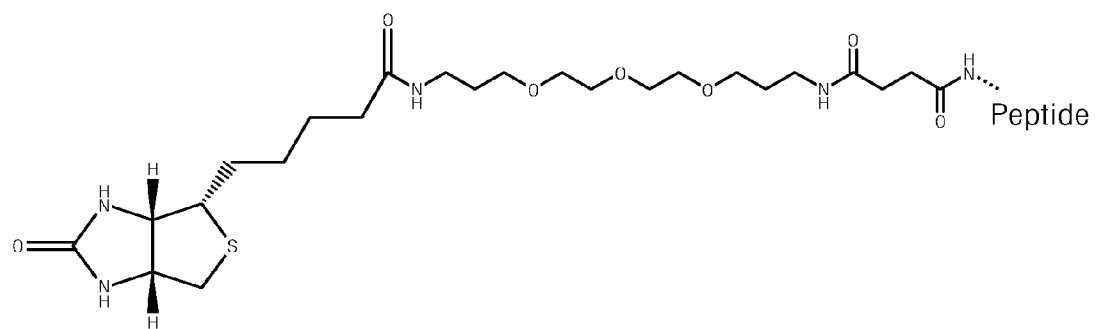
FIG. 2 shows a structural formula of the amino-terminal biotinyl-4,7,10-trioxa-13-tridecaneamineamine succinic acid (biotinyl-Ttds) linker of the thrombin-specific ligand biotinyl-Ttds-D-Phe-Pro-Arg-H and of the factor Xa-specific ligand biotinyl-Ttds-D-Arg-Gly-Arg-H.

FIG. 2 shows a structural formula of the amino-terminal biotinyl-4,7,10-trioxa-13-tridecaneamineamine succinic acid (biotinyl-Ttds) linker of the thrombin-specific ligand biotinyl-Ttds-D-Phe-Pro-Arg-H and of the factor Xa-specific ligand biotinyl-Ttds-D-Arg-Gly-Arg-H.

Figure 3:
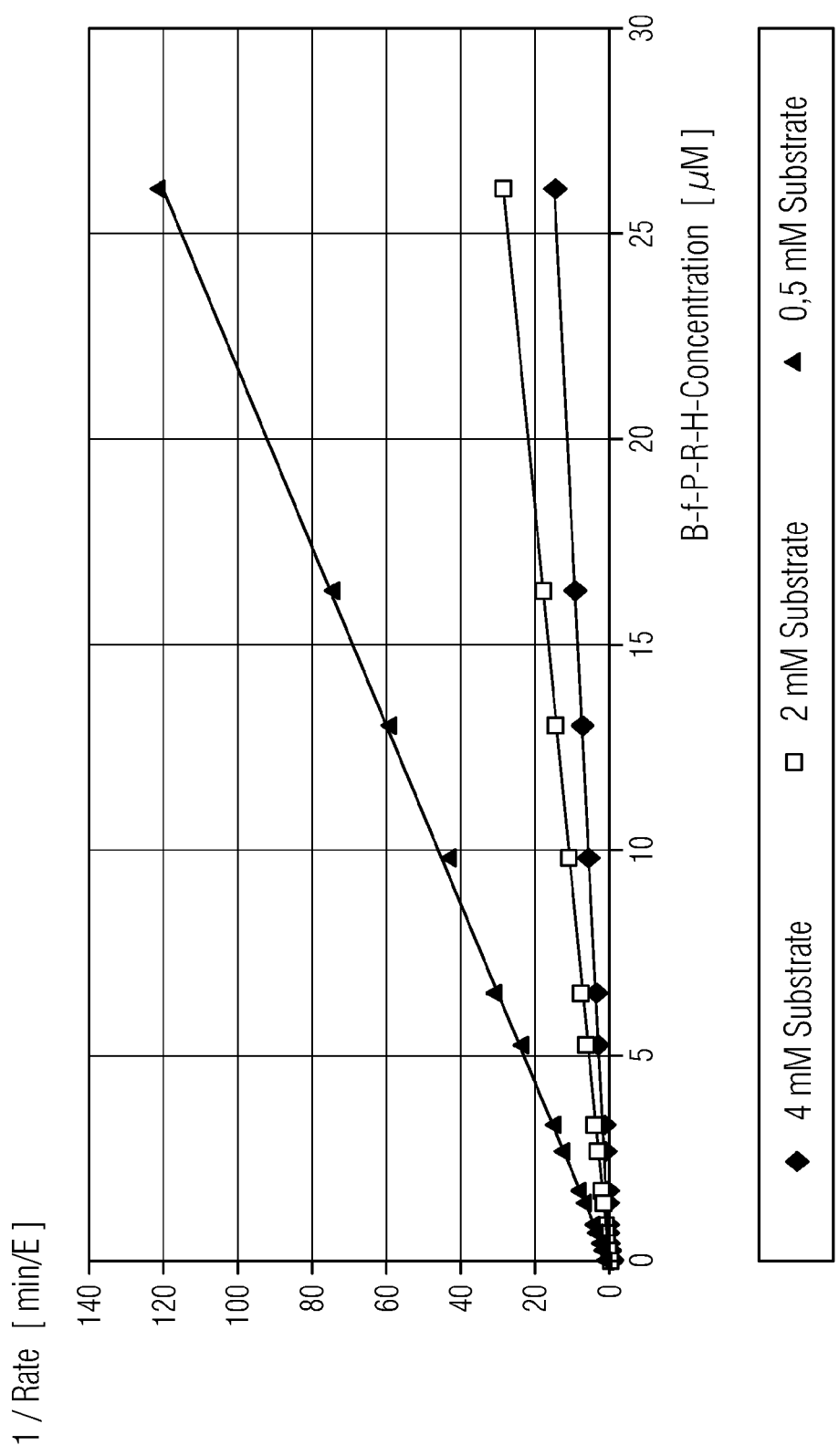
FIG. 3 shows determination of the thrombin binding constant of biotinyl-Ttds-D-Phe-Pro-Arg-H (B-f-P—R—H).

FIG. 3 shows determination of the thrombin binding constant of biotinyl-Ttds-D-Phe-Pro-Arg-H (B-f-P—R—H). Representation of the reciprocal reaction rate as a function of the ligand concentration at chromogenic substrate concentrations of 4, 2 and 0.5 mM in a thrombin assay according to example 2.

Figure 4:
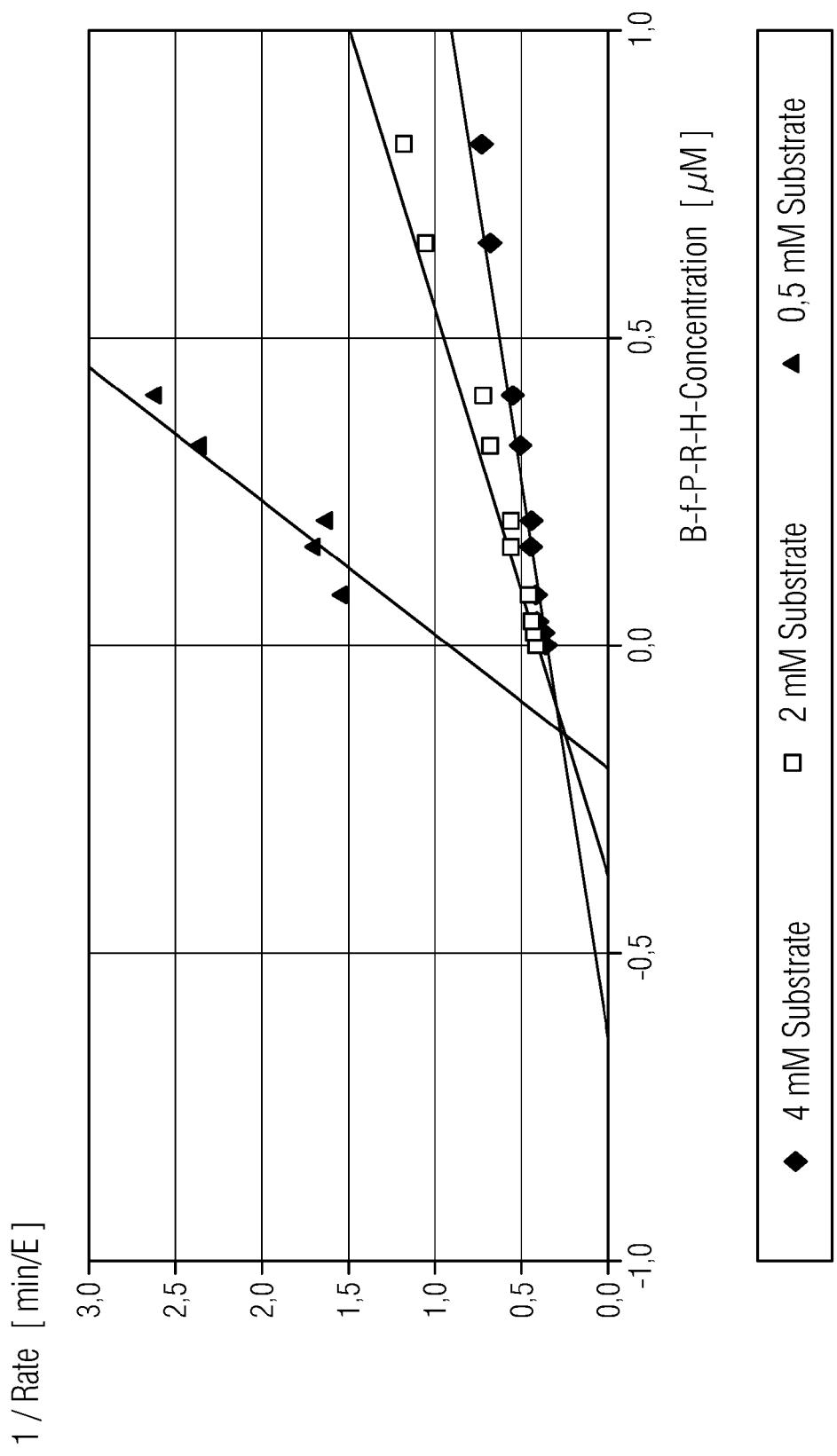
FIG. 4 shows determination of the thrombin binding constant of biotinyl-Ttds-D-Phe-Pro-Arg-H (B-f-P—R—H). Enlarged detail of FIG. 3.

FIG. 4 shows determination of the thrombin binding constant of biotinyl-Ttds-D-Phe-Pro-Arg-H (B-f-P—R—H). Enlarged detail of FIG. 3.

Figure 5:
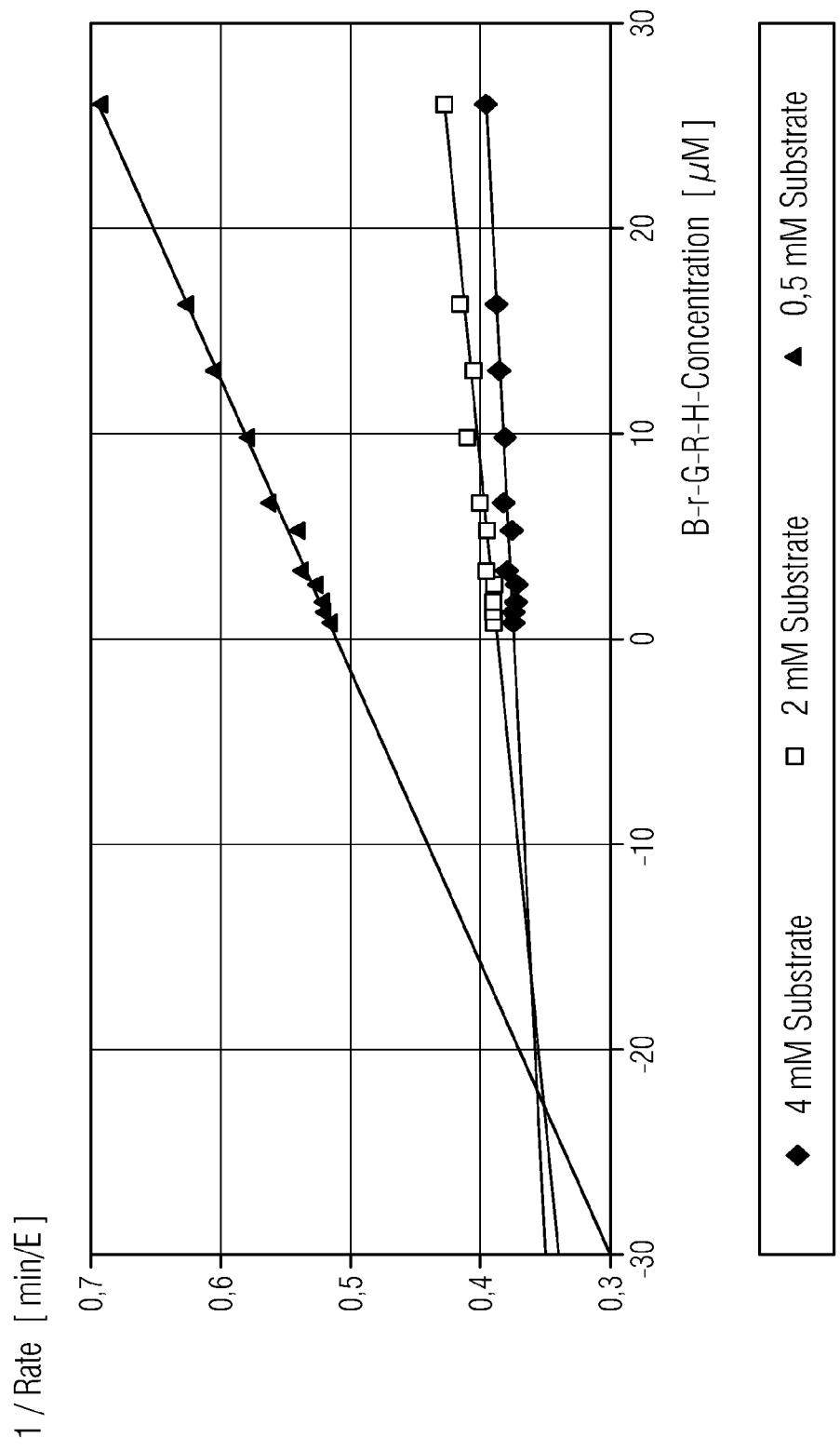
FIG. 5 shows determination of the thrombin binding constant of biotinyl-Ttds-D-Arg-Gly-Arg-H (B-r-G-R—H).

FIG. 5 shows determination of the thrombin binding constant of biotinyl-Ttds-D-Arg-Gly-Arg-H (B-r-G-R—H). Representation of the reciprocal reaction rate as a function of the ligand concentration at chromogenic substrate concentrations of 4, 2 and 0.5 mM in a thrombin assay according to example 2.

Figure 6:
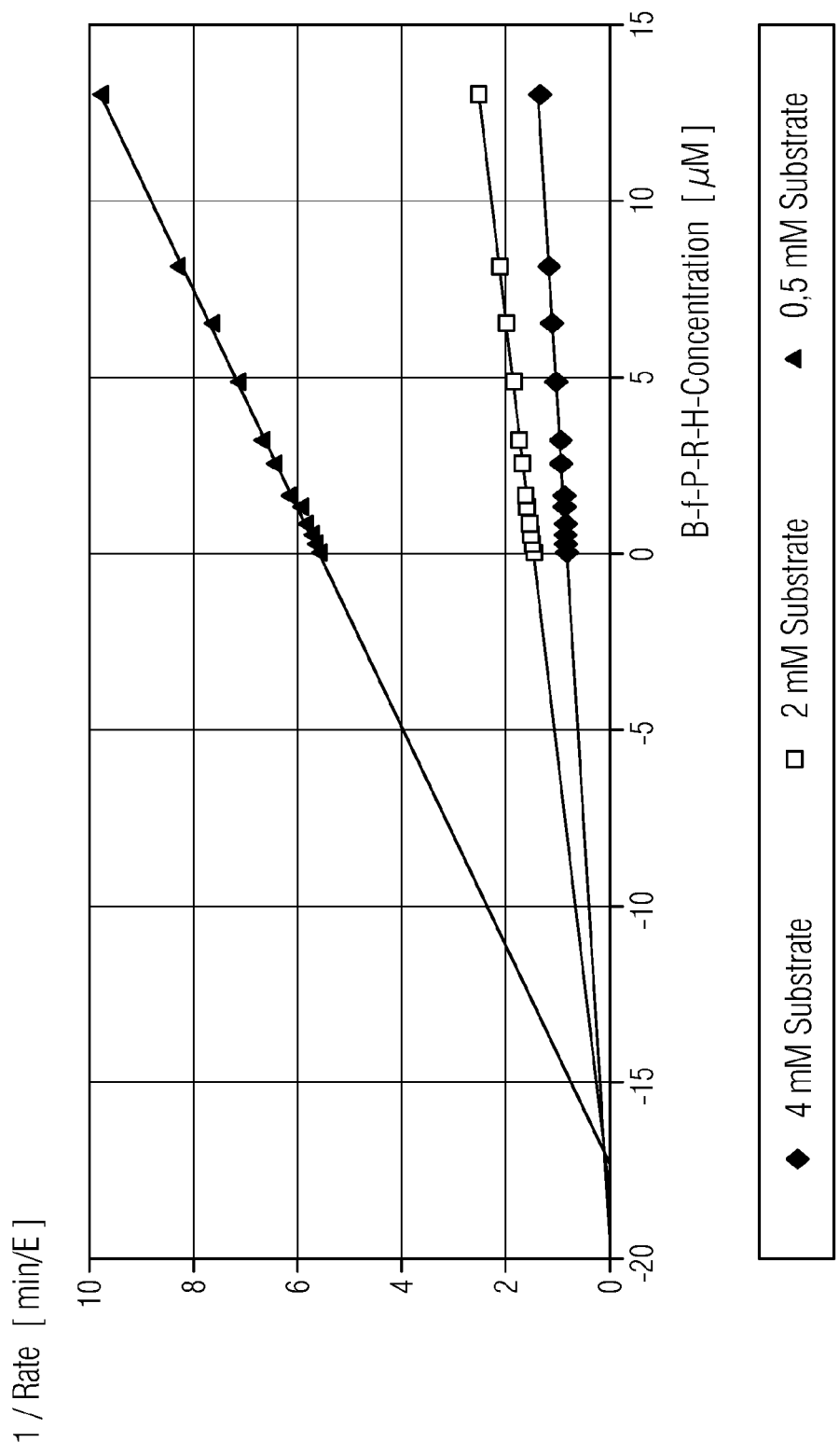
FIG. 6 shows determination of the F Xa binding constant of biotinyl-Ttds-D-Phe-Pro-Arg-H (B-f-P—R—H).

FIG. 6 shows determination of the F Xa binding constant of biotinyl-Ttds-D-Phe-Pro-Arg-H (B-f-P—R—H). Representation of the reciprocal reaction rate as a function of the ligand concentration at chromogenic substrate concentrations of 4, 2 and 0.5 mM in an F Xa assay according to example 3.

Figure 7:
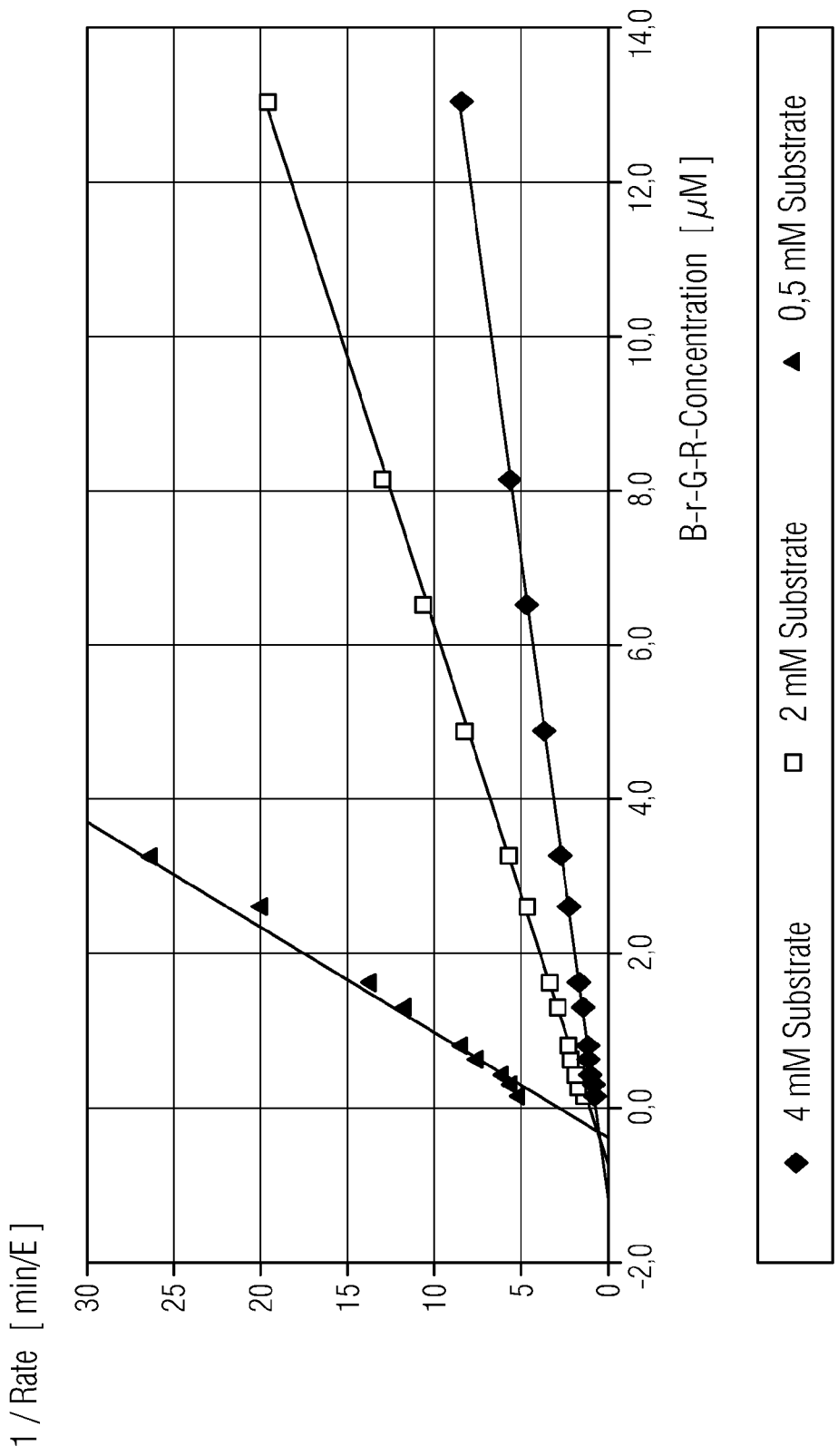
FIG. 7 shows determination of the F Xa binding constant of biotinyl-Ttds-D-Arg-Gly-Arg-H (B-r-G-R—H).

FIG. 7 shows determination of the F Xa binding constant of biotinyl-Ttds-D-Arg-Gly-Arg-H (B-r-G-R—H). Representation of the reciprocal reaction rate as a function of the ligand concentration at chromogenic substrate concentrations of 4, 2 and 0.5 mM in an F Xa assay according to example 3.

Figure 8:
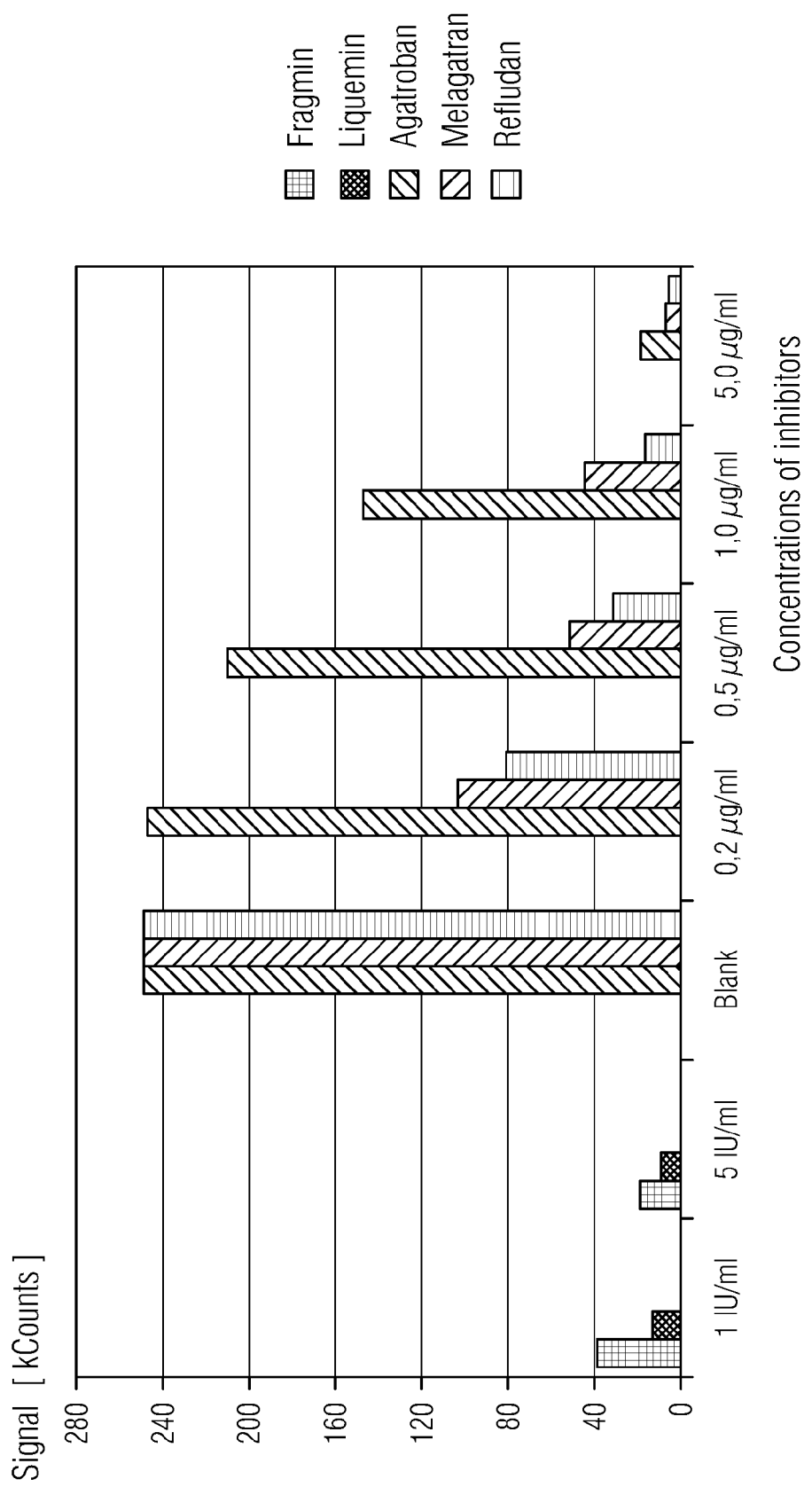
FIG. 8 shows chemiluminescence signal production in standard human plasma with various concentrations of the thrombin inhibitors fragmin, liquemin, argatroban, melagatran and refludan (hirudin), with the ligand biotinyl-Ttds-D-Phe-Pro-Arg-H (B-f-P—R—H) being employed in conjunction with thrombin-coated Chemibeads and streptavidin-coated Sensibeads.

FIG. 8 shows chemiluminescence signal production in standard human plasma with various concentrations of the thrombin inhibitors fragmin, liquemin, argatroban, melagatran and refludan (hirudin), with the ligand biotinyl-Ttds-D-Phe-Pro-Arg-H (B-f-P—R—H) being employed in conjunction with thrombin-coated Chemibeads and streptavidin-coated Sensibeads.

Figure 9:
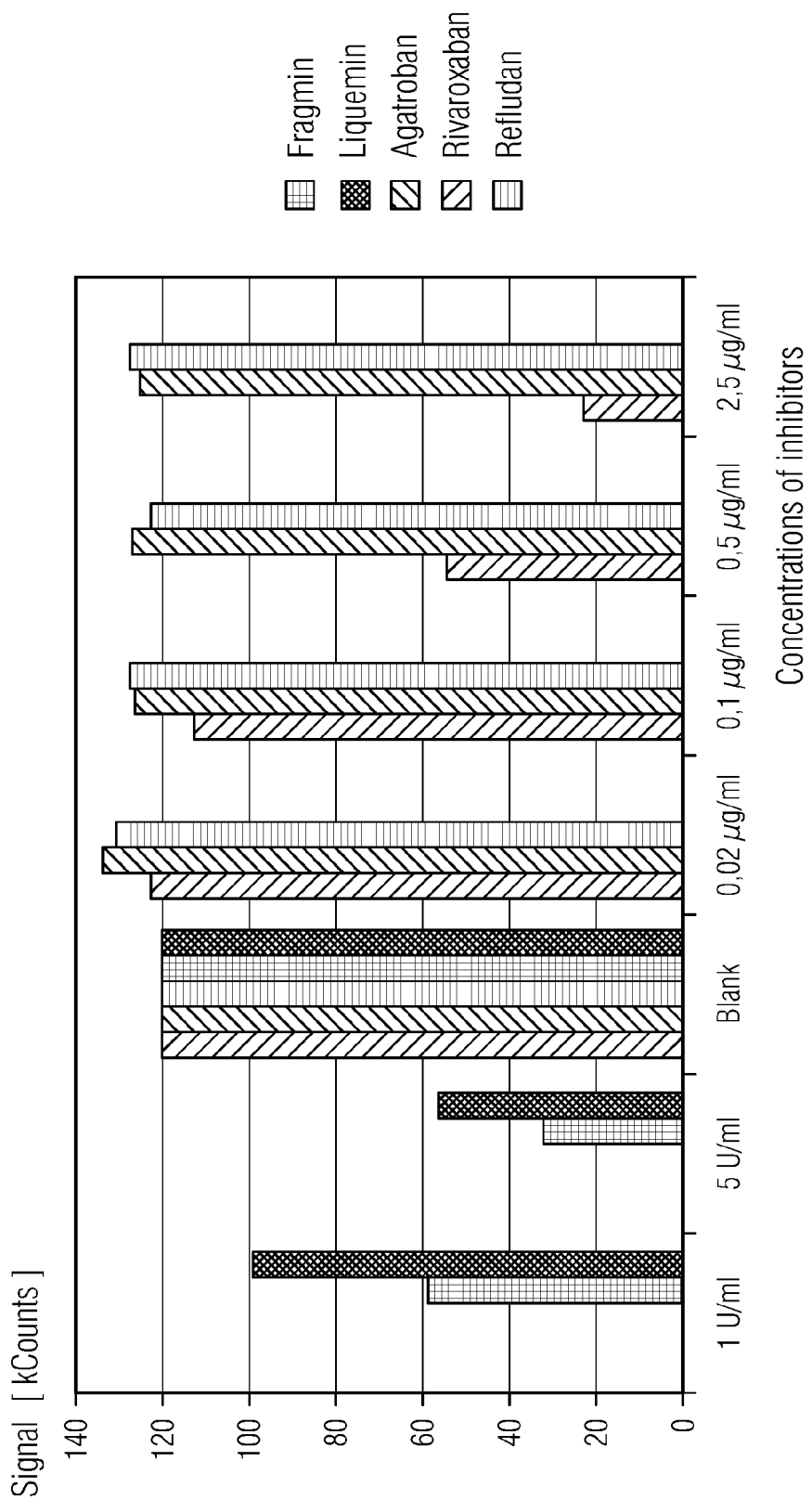
FIG. 9 shows chemiluminescence signal production in standard human plasma with various concentrations of the F Xa inhibitors fragmin, liquemin and rivaroxaban and of the thrombin inhibitors refludan (hirudin) and argatroban, with the ligand biotinyl-Ttds-D-Arg-Gly-Arg-H (B-r-G-R—H) being used in conjunction with anti-F Xa antibody-coated Chemibeads, F Xa and streptavidin-coated Sensibeads.

FIG. 9 shows chemiluminescence signal production in standard human plasma with various concentrations of the F Xa inhibitors fragmin, liquemin and rivaroxaban and of the thrombin inhibitors refludan (hirudin) and argatroban, with the ligand biotinyl-Ttds-D-Arg-Gly-Arg-H (B-r-G-R—H) being used in conjunction with anti-F Xa antibody-coated Chemibeads, F Xa and streptavidin-coated Sensibeads.

The following examples serve to illustrate the present invention and should not be construed as limitation.

Example 1

Synthesis of Thrombin and Factor Xa biotinyl-Ttds-peptide Aldehyde Ligands

The peptide aldehydes -D-Phe-Pro-Arg-H (see Claeson, G., Blood Coagulation and Fibrinolysis 5, 1994, page 417) and -D-Arg-Gly-Arg-H (cf. Claeson, G., Blood Coagulation and Fibrinolysis 5, 1994, page 426) were synthesized on a solid phase, extended with a Ttds spacer (Ttds=4,7,10-trioxa-1,13-tridecanediaminosuccinic acid (Bartos, A. et al., 2009, Biopolymers 92(2), 110-115)), and provided with biotin. The compound biotinyl-Ttds-D-Phe-Pro-Arg-H has a molecular weight of 930.15 g/mol and is abbreviated to B-f-P—R—H hereinbelow. The compound biotinyl-Ttds-D-Arg-Gly-Arg-H has a molecular weight of 899.10 g/mol and is abbreviated to B-r-G-R—H hereinbelow. The peptide aldehydes were removed from the solid phase with trifluoroacetic acid. The compounds were stored at −20° C. in a lyophilized form. The structure of the biotin linker is depicted in FIG. 2.

Example 2

Determination of the Thrombin Binding Constants of the Peptide Aldehyde Ligands

The kinetic data of the peptide aldehyde ligands were determined in chromogenic assay formats by measuring the rate of hydrolysis of chromogenic peptide substrates which compete with the peptide aldehyde ligands for binding to the active site of the particular enzyme, at various substrate concentrations and peptide aldehyde-ligand concentrations. The binding constant (Ki) was determined by a known method (Dixon, M., 1953, Biochem J, 55, 170-171).

The thrombin binding constant was determined using the reagents of the hirudin activity assay from Siemens Healthcare Diagnostics. The hirudin activity assay comprises a lyophilized thrombin reagent consisting of bovine thrombin, a heparin inhibitor and aprotinin, a lyophilized chromogenic substrate reagent with a concentration of 4 mmol/l tos-Gly-Pro-Arg-ANBA-IPA (tosylglycyl-L-propyl-arginyl-5-amino-2-nitrobenzoyliso-propylamide) after reconstitution. The thrombin reagent was reconstituted in buffer solution (trishydroxymethylamino-methane, NaCl, pH 8.2). Dilutions of the substrate reagent were prepared with deionized water. The peptide aldehyde ligands prepared according to example 1 were dissolved in water and used as sample. The B-r-G-R—H ligand was used in a concentration range from 26.1 to 0.815 μM. The B-f-P—R—H ligand was used in a concentration range from 26.1 to 0 μM. The assays were carried out automatically in a BCS® XP coagulation analyzer (Siemens Healthcare Diagnostics, Marburg, Germany).

A reaction mix was mixed together as follows:
30 μl of sample (peptide aldehyde ligand B-r-G-R—H or B-f-P—R—H),
150 μl of thrombin reagent,
50 μl of chromogenic substrate reagent (tos-Gly-Pro-Arg-ABNA-IPA).

The reaction rate in mE/min was determined on the basis of the increase in optical density of the reaction mix at a wavelength of 405 nm. For this, the optical density of the reaction mixes was determined in time intervals of from 15 to 40 seconds for the B-f-P—R—H peptide aldehyde ligand or 5-16 seconds for the B-r-G-R—H peptide aldehyde ligand.

Reversibly and irreversibly binding ligands can be distinguished by their reaction kinetics. Plotting 1/v, where v is the reaction rate, as a function of the ligand concentration (i) at a constant concentration (S) of a cleavable substrate produces a line. When using two or more different substrate concentrations ($S_1, S_2 \ldots S_N$), said lines intersect at a single point. The x axis value of this point corresponds to $-K_i$, with $K_i$ corresponding to the binding constant, see, for example, Klebe, G., Wirkstoffdesign, $2^{nd}$ edition, Spektrum Akademischer Verlag, Heidelberg, Germany, 2009, pages 52-62 and Dixon, M., 1953, Biochem J, 55, 170-171. With an irreversible inhibition, the curves meet at a single point on the x axis, which again corresponds to $-K_i$.

Table 2 depicts the concentrations of the peptide aldehyde ligand B-f-P—R—H employed in the reaction mix and the reciprocals of the reaction rates obtained with the various concentrations of the chromogenic substrate.

TABLE 2

| $C_{B\text{-}f\text{-}P\text{-}R\text{-}H}$ | 1/Reaction rate [min/E] | | |
|---|---|---|---|
| [μM] | $C_{substrate}$ = 4 mM | $C_{substrate}$ = 2 mM | $C_{substrate}$ = 0.5 mM |
| 26.08696 | 14.58931 | 28.40843 | 121.67418 |
| 16.30435 | 9.30221 | 18.08682 | 74.54798 |
| 13.04348 | 7.61108 | 14.42763 | 59.11941 |
| 9.78261 | 5.84267 | 11.17905 | 43.90039 |
| 6.52174 | 4.08943 | 7.85565 | 32.28213 |
| 5.21739 | 3.25123 | 6.16548 | 24.75736 |
| 3.26087 | 2.13002 | 4.02645 | 15.77139 |
| 2.60870 | 1.77535 | 3.36951 | 13.19230 |

TABLE 2-continued

| $C_{B\text{-}f\text{-}P\text{-}R\text{-}H}$ | 1/Reaction rate [min/E] | | |
|---|---|---|---|
| [μM] | $C_{substrate}$ = 4 mM | $C_{substrate}$ = 2 mM | $C_{substrate}$ = 0.5 mM |
| 1.63043 | 1.18258 | 2.16372 | 8.49129 |
| 1.30435 | 0.99739 | 1.79279 | 7.17521 |
| 0.81522 | 0.72743 | 1.16912 | 4.77479 |
| 0.65217 | 0.67366 | 1.02929 | 4.16189 |
| 0.40761 | 0.53337 | 0.70084 | 2.64461 |
| 0.32609 | 0.50125 | 0.66133 | 2.38165 |
| 0.20380 | 0.42975 | 0.50607 | 1.63785 |
| 0.16304 | 0.43955 | 0.52101 | 1.71097 |
| 0.08152 | 0.41427 | 0.45943 | 1.56479 |
| 0.04076 | 0.39301 | 0.42471 | 1.74741 |
| 0.02038 | 0.38457 | 0.41376 | 1.86941 |
| 0 | 0.38254 | 0.41286 | 1.93034 |

The regression curves were plotted in the linear region of the graphs of 1/reaction rate as a function of the ligand concentration ($C_{B\text{-}f\text{-}P\text{—}R\text{—}H}$) at the various substrate concentrations (FIGS. 3 and 4). For $C_{substrate}$=0.5 mM, the concentrations from 0 to 0.04076 μM were not in the linear region and were therefore excluded. Three $K_i$ values were calculated from the intersections of the regression curves and from these an average $K_i$ value and the intersections of the graphs were then calculated. From the $K_i$ values obtained in this way, the average $K_i$ value was calculated (table 3). Since the intersections of the regression curves are not on the x axis, binding of the peptide aldehyde with thrombin is reversible. The average thrombin binding constant $K_{iM}$ of the peptide aldehyde ligand B-f-P—R—H is 0.131 μmol ($1.31 \times 10^{-7}$ mol). Since the binding constants of the relevant medicaments (therapeutically effective and suitable thrombin inhibitors) are larger, the compound according to the method described, using thrombin as active coagulation enzyme, is suitable for detecting high-affinity thrombin inhibitors.

TABLE 3

Thrombin binding constant ($K_i$) of B-f-P-R-H

| $C_{substrate}$ (mM) | Slope (min/E μM) | Intersect (min/E) | $R^2$ | $K_i$ (μM) |
|---|---|---|---|---|
| 4 | 0.5500 | 0.3497 | 0.9997 | $K_{i1\&2}$ = 0.106 |
| 2 | 1.0812 | 0.04059 | 0.9997 | $K_{i1\&3}$ = 0.141 |
| 0.5 | 4.5718 | 0.9175 | 0.9994 | $K_{i2\&3}$ = 0.147 |
| | | | average $K_i$: | $K_{iM}$ = 0.131 |

Table 4 indicates the concentrations of the peptide aldehyde ligand B-r-G-R—H employed in the reaction mix and the reciprocals of the reaction rates obtained with the various concentrations of the chromogenic substrate.

TABLE 4

| $C_{B\text{-}r\text{-}G\text{-}R\text{-}H}$ | 1/Reaction rate [min/E] | | |
|---|---|---|---|
| [μM] | $C_{substrate}$ = 4 mM | $C_{substrate}$ = 2 mM | $C_{substrate}$ = 0.5 mM |
| 26.08696 | 0.39497 | 0.42847 | 0.69034 |
| 16.30435 | 0.38645 | 0.41405 | 0.62639 |
| 13.04348 | 0.38853 | 0.40320 | 0.60905 |
| 9.78261 | 0.38047 | 0.41056 | 0.58021 |
| 6.52174 | 0.38410 | 0.40077 | 0.56372 |
| 5.21739 | 0.37614 | 0.39456 | 0.54078 |
| 3.26087 | 0.38074 | 0.39679 | 0.53851 |
| 2.60870 | 0.37303 | 0.38756 | 0.52827 |
| 1.63043 | 0.37478 | 0.38938 | 0.52245 |
| 1.30435 | 0.37579 | 0.39024 | 0.52112 |
| 0.81522 | 0.37556 | 0.38842 | 0.51597 |

The regression curves were plotted in the linear region of the graphs of 1/reaction rate as a function of the ligand concentration ($C_{B-r-G-R-H}$) at the various substrate concentrations (FIG. 5). Three $K_i$ values were calculated from the intersections of the regression curves and from these an average $K_i$ value and the intersections of the graphs were then calculated. From the $K_i$ values obtained in this way, the average $K_i$ value was calculated (table 5). Since the intersections of the regression curves are not on the x axis, binding of the peptide aldehyde with thrombin is reversible. The average thrombin binding constant $K_{iM}$ of the peptide aldehyde ligand B-r-G-R—H is 20.9 μmol ($2.09 \times 10^{-5}$ mol). The ligand is therefore suitable according to the method described, using thrombin as active coagulation enzyme, for determining also low-affinity thrombin inhibitors.

TABLE 5

Thrombin binding constant ($K_i$) of B-r-G-R-H

| $C_{substrate}$ (mM) | Slope (min/E μM) | Intersect (min/E) | $R^2$ | $K_i$ (μM) |
|---|---|---|---|---|
| 4 | 0.000805 | 0.3746 | 0.8520 | $K_{i1\&2}$ = 17.4 |
| 2 | 0.001572 | 0.3880 | 0.9246 | $K_{i1\&3}$ = 22.3 |
| 0.5 | 0.006964 | 0.5122 | 0.9544 | $K_{i2\&3}$ = 23.0 |
| | | | average $K_i$: | $K_{iM}$ = 20.9 |

Example 3

Determination of the F Xa Binding Constants of the Peptide Aldehyde Ligands

The F Xa binding constant was determined using the reagents of the Berichrom® heparin assay from Siemens Healthcare Diagnostics. The Berichrom® heparin assay consists of:
an F Xa reagent consisting of a lyophilized plasma fraction containing factor Xa, and additives such as Tris, NaCl, EDTA and preservatives,
a chromogenic substrate reagent (Z-D-Leu-Gly-Arg-ANBA-methyl-amide),
a dilution reagent for reconstitution, and
a dextran sulfate reagent consisting of lyophilized dextran sulfate.

After reconstitution in 10 ml of dilution reagent, the dextran sulfate concentration is 0.02 g/l. The F Xa reagent is reconstituted with the reconstituted dextran sulfate reagent. The substrate reagent, after constitution with 2 ml of deionized water, contains 4 mmol/l Z-D-Leu-Gly-Arg-ANBA-methyl-amide. Dilutions of the substrate reagent were prepared with deionized water. The peptide aldehyde ligands prepared according to example 1 were dissolved in water and used as sample. The assays were carried out automatically in a BCS® XP coagulation analyzer (Siemens Healthcare Diagnostics, Marburg, Germany).

A reaction mix was mixed together as follows:
20 μl of water,
15 μl of sample (peptide aldehyde ligand B-r-G-R—H or B-f-P—R—H),
15 μl of water,
150 μl of F Xa reagent,
30 μl of substrate reagent (Z-D-Leu-Gly-Arg-ANBA-methyl-amide).
The reaction rate in mE/min was determined on the basis of the increase in optical density of the reaction mix at a wavelength of 405 nm. For this, the optical density of the reaction mixes was determined in a time interval from 10 to 70 seconds.

Table 6 depicts the concentrations of the peptide aldehyde ligand B-f-P—R—H employed in the reaction mix and the reciprocals of the reaction rates obtained with the various concentrations of the chromogenic substrate.

TABLE 6

| $C_{B\text{-}f\text{-}P\text{-}R\text{-}H}$ | 1/Reaction rate [min/E] | | |
|---|---|---|---|
| [μM] | $C_{substrate}$ = 4 mM | $C_{substrate}$ = 2 mM | $C_{substrate}$ = 0.5 mM |
| 13.04348 | 1.35879 | 2.49937 | 9.73911 |
| 8.15217 | 1.17310 | 2.14879 | 8.37740 |
| 6.52174 | 1.10558 | 1.97908 | 7.61262 |
| 4.89130 | 1.02567 | 1.83999 | 7.08399 |
| 3.26087 | 0.94477 | 1.71517 | 6.66273 |
| 2.60870 | 0.93172 | 1.67166 | 6.44104 |
| 1.63043 | 0.90212 | 1.59083 | 6.26347 |
| 1.30435 | 0.87349 | 1.56215 | 5.95893 |
| 0.81522 | 0.84935 | 1.52113 | 5.86778 |
| 0.65217 | 0.85137 | 1.50973 | 5.78490 |
| 0.40761 | 0.83380 | 1.48916 | 5.69390 |
| 0.32609 | 0.83198 | 1.48552 | 5.68996 |
| 0.20380 | 0.82383 | 1.47333 | 5.61861 |
| 0.16304 | 0.83329 | 1.48487 | 5.67486 |
| 0.10190 | 0.81565 | 1.46315 | 5.61945 |
| 0.08152 | 0.82180 | 1.46678 | 5.57154 |
| 0.04076 | 0.81738 | 1.45442 | 5.56930 |
| 0.02038 | 0.81918 | 1.45743 | 5.56461 |
| 0.01019 | 0.82168 | 1.45734 | 5.61679 |
| 0 | 0.83042 | 1.47267 | 5.68282 |

The regression curves were plotted in the linear region of the graphs of 1/reaction rate as a function of the ligand concentration ($C_{B-f-P-R-H}$) at the various substrate concentrations (FIG. 6). Three $K_i$ values were calculated from the intersections of the regression curves and from these an average $K_i$ value and the intersections of the graphs were then calculated. From the $K_i$ values obtained in this way, the average $K_i$ value was calculated (table 7). Since the intersections of the regression curves are not on the x axis, binding of the peptide aldehyde with F Xa is reversible. The average F Xa binding constant $K_{iM}$ of the peptide aldehyde ligand B-f-P—R—H is 16.9 μmol ($1.69 \times 10^{-5}$ mol). The ligand is therefore suitable according to the method described, using F Xa as active coagulation enzyme, for determining low-affinity F Xa inhibitors.

TABLE 7

F Xa binding constant ($K_i$) of B-f-P-R-H

| $C_{substrate}$ (mM) | Slope (min/E μM) | Intersect (min/E) | $R^2$ | $K_i$ (μM) |
|---|---|---|---|---|
| 4 | 0.0421 | 0.8202 | 0.9975 | $K_{i1\&2}$ = 16.6 |
| 2 | 0.0806 | 1.4588 | 0.9987 | $K_{i1\&3}$ = 17.1 |
| 0.5 | 0.3216 | 5.5934 | 0.9965 | $K_{i2\&3}$ = 17.2 |
| | | | average $K_i$: | $K_{iM}$ = 16.9 |

Table 8 depicts the concentrations of the peptide aldehyde ligand B-r-G-R—H employed in the reaction mix and the reciprocals of the reaction rates obtained with the various chromogenic substrate concentrations.

TABLE 8

| $C_{B-r-G-R-H}$ | 1/Reaction rate [min/E] | | |
|---|---|---|---|
| [µM] | $C_{substrate}$ = 4 mM | $C_{substrate}$ = 2 mM | $C_{substrate}$ = 0.5 mM |
| 13.04348 | 8.46963 | 19.61291 | 98.11308 |
| 8.15217 | 5.66889 | 12.99196 | 62.32312 |
| 6.52174 | 4.81865 | 10.44658 | 52.69400 |
| 4.89130 | 3.74536 | 8.24448 | 37.79438 |
| 3.26087 | 2.72840 | 5.52006 | 26.41568 |
| 2.60870 | 2.27442 | 4.62654 | 20.14413 |
| 1.63043 | 1.67882 | 3.14700 | 13.97126 |
| 1.30435 | 1.47587 | 2.80172 | 12.04614 |
| 0.81522 | 1.17709 | 2.11479 | 8.40260 |
| 0.65217 | 1.09950 | 1.97479 | 7.75440 |
| 0.40761 | 0.92591 | 1.65890 | 6.40799 |
| 0.32609 | 0.90610 | 1.61219 | 6.12959 |
| 0.20380 | 0.82623 | 1.45744 | 5.52072 |

The regression curves were plotted in the linear region of the graphs of 1/reaction rate as a function of the ligand concentration ($C_{B-r-G-R-H}$) at the various substrate concentrations (FIG. 7). Three $K_i$ values were calculated from the intersections of the regression curves and from these an average $K_i$ value and the intersections of the graphs were then calculated. From the $K_i$ values obtained in this way, the average $K_i$ value was calculated (table 9). Since the intersections of the regression curves are not on the x axis, binding of the peptide aldehyde with F Xa is reversible. The average F Xa binding constant $K_{iM}$ of the peptide aldehyde ligand B-r-G-R—H is 0.332 µmol ($3.32 \times 10^{-7}$ mol). Since the binding constants of the relevant medicaments (therapeutically effective and suitable F Xa inhibitors) are larger, the compound according to the method described, using F Xa as active coagulation enzyme, is suitable for detecting high-affinity F Xa inhibitors.

TABLE 9

| F Xa binding constant ($K_i$) of B-r-G-R-H | | | | |
|---|---|---|---|---|
| $C_{substrate}$ (mM) | Slope (min/E µM) | Intersect (min/E) | $R^2$ | $K_i$ (µM) |
| 4 | 0.6037 | 0.7187 | 0.9992 | $K_{i1\&2}$ = 0.358 |
| 2 | 1.4375 | 1.0169 | 0.9992 | $K_{i1\&3}$ = 0.321 |
| 0.5 | 7.3110 | 2.8743 | 0.9987 | $K_{i2\&3}$ = 0.316 |
| | | | average $K_i$: | $K_{iM}$ = 0.332 |

Example 4

Method of the Invention for Determining Thrombin Inhibitors by Means of LOCI Reagents The samples used were standard human plasma and standard human plasma to which increasing concentrations of direct (hirudin, melagatran, argatroban) or indirect (liquemin, fragmin) thrombin inhibitors were added.

The signal-producing system used was the LOCI® system consisting of a chemiluminescent compound (2-(4-(N,N, ditetradecyl)-anilino-3-phenyl thioxene) and a photosensitizer (bis-(trihexyl)-silicon-t-butyl-phthalocyanine). Both the chemiluminescent compound and the photosensitizer are coupled to latex particles. The terms "Chemibeads", for the particles coated with the chemiluminescent compound, and "Sensibeads", for the particles coated with the photosensitizer, are also used hereinbelow. The LOCI technology used herein is based on the latex particle-coupled chemiluminescent compound (Chemibeads) and the latex particle-coupled photosensitizer (Sensibeads), through binding to an analyte, being brought into close spatial proximity to one another, and as a result singlet oxygen generated by the photosensitizer can excite the chemiluminescent compound.

The Chemibeads used herein were additionally coated with bovine thrombin. For this, bovine thrombin was covalently linked to the latex particles. The Sensibeads used herein were additionally coated with streptavidin.

The ligand used was the biotinylated peptide aldehyde biotinyl-Ttds-D-Phe-Pro-Arg-H (B-f-P—R—H).

In the absence of a thrombin inhibitor, the ligand binds, via its biotin residue, to the streptavidin-coated Sensibeads and, via its peptide moiety, to the thrombin-coated Chemibeads, and a chemiluminescence signal is generated (see also FIG. 1). In the presence of a thrombin inhibitor which competes with the ligand for binding to the thrombin-coated Chemibeads but which cannot bind to the Sensibeads, the chemiluminescence signal is inversely proportional to the thrombin inhibitor concentration.

In each case 2 µl of sample, 10 µl of the fibrin polymerization inhibitor peptide glycine-proline-arginine-proline (10 mg/ml), 20 µl of Chemibeads (400 µg/ml) and 10 µl of the ligand (1.25 µM) were combined and incubated for 6 minutes. After addition of 20 µl of Sensibeads (600 µg/ml) and incubation for 10 minutes, the mix was filled with water to 250 µl and the chemiluminescence signal was measured. As FIG. 8 indicates, the chemiluminescence signal is reduced as a function of the type and concentration of the direct thrombin inhibitors metered in. Metered-in heparins (liquemin, fragmin), which inhibit thrombin indirectly, also result in a distinct reduction of the chemiluminescence signal.

Example 5

Method of the Invention for Determining Factor Xa Inhibitors by Means of LOCI Reagents The samples used were standard human plasma and standard human plasma to which increasing concentrations of direct or indirect thrombin inhibitors (hirudin, argatroban, liquemin) or factor Xa inhibitors (rivaroxaban, liquemin, fragmin) were added.

The signal-producing system used was the LOCI system according to example 4.

The Chemibeads used herein were additionally coated with a commercially available polyclonal antibody to F Xa. For this, the antibody was linked covalently to the latex particles in a coupling ratio of 10 mg of antibody to 50 ng of particles. The Sensibeads used herein were additionally coated with streptavidin.

The ligand used was the biotinylated peptide aldehyde biotinyl-Ttds-D-Arg-Gly-Arg-H (B-r-G-R—H).

In the absence of an F Xa inhibitor, the ligand binds, via its biotin residue, to the streptavidin-coated Sensibeads and, via its peptide moiety, to the F Xa which itself binds to the antibody-coated Chemibeads, and a chemiluminescence signal is generated (see also FIG. 1). In the presence of an F Xa inhibitor which competes with the ligand for binding to the F Xa-coated Chemibeads but which cannot bind to the Sensibeads, the chemiluminescence signal is inversely proportional to the F Xa inhibitor concentration (e.g. rivaroxaban). In the presence of a thrombin inhibitor (e.g. argatroban or hirudin), however, the signal is not reduced, since the thrombin inhibitor cannot displace the ligand.

10 µl of a reagent containing human F Xa (approx. 1000 IU/l) and fibrin polymerization inhibitor peptide glycine-proline-arginine-proline (10 mg/ml) were admixed with 2 µl of sample, 20 µl of Chemibeads (400 µg/ml) and 10 µl of the ligand (6 μM) and incubated for 5 minutes. After addition of 60 μl of Sensibeads (200 μg/ml) and incubation for 10 minutes, the mix was filled with water to 260 μl and the chemiluminescence signal was measured. As FIG. 9 indicates, the chemiluminescence signal is reduced as a function of the type and concentration of the direct F Xa and thrombin inhibitors metered in. Metered-in heparins (liquemin, fragmin), which inhibit F Xa indirectly, also result in a distinct reduction of the chemiluminescence signal.

The invention claimed is:

1. A method of determining an inhibitor of a proteolytically active coagulation factor in a sample, comprising the steps of:
   a) providing and incubating a reaction mix comprising
      i. an aliquot of the sample,
      ii. a defined amount of a proteolytically active coagulation factor,
      iii. at least one ligand which binds to the active site of the proteolytically active coagulation factor but is not cleaved by the latter at a peptide bond,
      iv. a first and a second component of a signal-producing system which act together in such a way that a detectable signal is generated when said first and second components of said signal-producing system are brought into close proximity to each other, and wherein the proteolytically active coagulation factor is associated with the first component of the signal-producing system or will be associated therewith during incubation, and wherein the ligand is associated with the second component of the signal-producing system or will be associated therewith during incubation;
   b) measuring the signal of the signal-producing system, wherein the amplitude of said signal is inversely proportional to the inhibitor concentration in the sample.

2. The method as claimed in claim 1, wherein the ligand which binds to the active site of the proteolytically active coagulation factor has a binding affinity of Ki=from $10^{-13}$ to $10^{-4}$ M to the proteolytically active coagulation factor.

3. The method as claimed in claim 1, wherein the first and second components of the signal-producing system each comprise a particulate solid phase, and wherein agglutination of the particulate solid phases in the reaction mix is measured.

4. The method as claimed in claim 1, wherein the first component of the signal-producting system is a chemiluminescent agent and the second component of the signal-producting system is a photosensitizer or vice versa, and wherein chemiluminescence in the reaction mix is measured.

5. The method as claimed in claim 4, wherein the chemiluminescent agent is associated with a first particulate solid phase and/or the photosensitizer is associated with a second particulate solid phase.

6. The method as claimed in claim 1, wherein the ligand has a first binding partner A of a first binding pair A/B, and wherein the second component of the signal-producing system has the second binding partner B of the first binding pair A/B, and wherein the ligand, due to binding of the binding partners A and B, is associated with the second component of the signal-producing system or will be associated therewith during incubation.

7. The method as claimed in claim 1, wherein the ligand is a peptide derivative.

8. The method as claimed in claim 1, wherein the ligand is a peptide derivative having a carboxy terminal group from the group consisting of aldehyde, ketone, trifluoromethyl ketone, α-ketocarboxylic acid, α-ketoamide, α-keto ester, ester, boronic acid, chloromethyl ketone, fluoride.

9. The method as claimed in claim 6, wherein the binding partners A and B are chosen such that they firm a binding pair A/B from the group consisting of FLAG Tag/anti-FLAG tag antibody, HIS tag/anti-HIS tag antibody, fluorescein/anti-fluorescein antibody, biotin/avidin, and biotin/streptavidin.

10. The method as claimed in claim 1, wherein the proteolytically active coagulation factor has a first binding partner X of a second binding pair X/Y, and wherein the second binding partner Y of the second binding pair X/Y is associated with the first component of the signal-producing system, and wherein the proteolytically active coagulation factor, due to binding of the binding partners X and Y, is associated with the first component of the signal-producing system or will be associated therewith during incubation.

11. The method as claimed in claim 1 for determining a thrombin inhibitor, wherein a reaction mix is provided and incubated which comprises a defined amount of the proteolytically active coagulation factor thrombin.

12. The method as claimed in claim 11, wherein a reaction mix is provided and incubated which comprises the peptide biotinyl-Ttds-D-Phe-Pro-Arg-H which binds reversibly to the active site of thrombin but is not cleaved thereby.

13. The method as claimed in claim 11 for determining a thrombin inhibitor from the group consisting of heparin, bivalirudin, hirudin, dabigatran, argatroban, melagatran, ximelagatran, lepirudin, MCC-977, SSR-182289, TGN-255, TGN-167, ARC-183 and odiparcil.

14. The method as claimed in claim 1 for determining a factor Xa inhibitor, wherein a reaction mix is provided and incubated which comprises a defined amount of the proteolytically active coagulation factor Xa.

15. The method as claimed in claim 14 for determining a factor Xa inhibitor from the group consisting of heparin, fondaparinux, ri varoxaban, apixaban, otamixaban, LY 517717, YM 153, DU-176b, DX-9065a and KFA-1982.

16. The method as claimed in claim 14, wherein a reaction mix is provided and incubated which comprises the peptide bionnyl-Ttds-D-Arg-Gly-Arg-H which binds reversibly to the active site of factor Xa but is not cleaved thereby.

17. A test kit for determining an inhibitor of a proteolytically active coagulation factor in a sample, said test kit comprising the following separate components:
   i. a first reagent comprising a defined amount of a proteolytically active coagulation factor;
   ii. a second reagent comprising at least one ligand which binds to the active site of the proteolytically active coagulation factor but is not cleaved by the latter at a peptide bond;
   iii. a third reagent comprising a first component of a signal-producing system, which component is associable with the proteolytically active coagulation factor from the first reagent; and
   iv. a fourth reagent comprising a second component of a signal-producing system, which component is associable with the ligand from the second reagent;
   wherein the first and second components of the signal-producing system act together in such a way that a detectable signal is generated when said first and second components of said signal-producing system are brought into close proximity to each other;
   wherein the test kit is configured for determining an inhibitor of a proteolytically active coagulation factor in a sample by providing and incubating a reaction mix comprising the components of the test kit and an aliquot of the sample, and measuring the signal of the signal-producing system, wherein the amplitude of said signal is inversely proportional to the inhibitor concentration in the sample.

* * * * *